United States Patent
O'Shaughnessy et al.

(10) Patent No.: US 6,986,785 B2
(45) Date of Patent: Jan. 17, 2006

(54) STENT BALLOON ASSEMBLY AND METHODS OF MAKING SAME

(75) Inventors: Donagh O'Shaughnessy, Galway (IE); Tony Neary, Galway (IE); James Coyle, Co Roscommon (IE); Jeremy Whitty, Newbridge (IE); Seamus Ledwith, Co Galway (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 627 days.

(21) Appl. No.: 10/137,934

(22) Filed: May 3, 2002

(65) Prior Publication Data

US 2003/0208255 A1 Nov. 6, 2003

(51) Int. Cl.
*A61M 25/10* (2006.01)
*A61F 2/06* (2006.01)

(52) U.S. Cl. .................. 623/1.11; 606/194; 606/108
(58) Field of Classification Search ............... 623/1.11, 623/1.12; 606/191, 194
See application file for complete search history.

(56) References Cited

U.S. PATENT DOCUMENTS

| | | | |
|---|---|---|---|
| 3,895,637 A | 7/1975 | Choy | |
| 5,116,318 A | 5/1992 | Hillstead | |
| 5,456,666 A * | 10/1995 | Campbell et al. | 606/194 |
| 5,487,730 A | 1/1996 | Marcadis et al. | |
| 5,653,690 A | 8/1997 | Booth et al. | |
| 5,720,726 A | 2/1998 | Marcadis et al. | |
| 5,836,965 A | 11/1998 | Jendersee et al. | |
| 5,868,703 A | 2/1999 | Bertolero et al. | |
| 5,935,135 A | 8/1999 | Bramfitt et al. | |
| 5,954,740 A | 9/1999 | Ravenscroft et al. | |
| 5,976,155 A | 11/1999 | Foreman et al. | |
| 5,976,181 A | 11/1999 | Whelan et al. | |
| 6,048,350 A | 4/2000 | Vrba | |
| 6,063,092 A * | 5/2000 | Shin | 606/194 |
| 6,110,180 A | 8/2000 | Foreman et al. | |
| 6,110,192 A | 8/2000 | Ravenscroft et al. | |
| 6,129,706 A | 10/2000 | Janacek | |
| 6,159,229 A | 12/2000 | Jendersee et al. | |
| 6,193,727 B1 | 2/2001 | Foreman et al. | |
| 6,258,099 B1 * | 7/2001 | Mareiro et al. | 606/192 |
| 6,289,568 B1 | 9/2001 | Miller et al. | |
| 6,309,402 B1 | 10/2001 | Jendersee et al. | |
| 2002/0049466 A1 | 4/2002 | Euateneuer et al. | |

FOREIGN PATENT DOCUMENTS

| | | |
|---|---|---|
| EP | 0 204 218 B1 | 8/1989 |
| EP | 0 834 293 A1 | 4/1998 |
| EP | 0 903 161 A2 | 3/1999 |
| EP | 0 903 161 A3 | 5/1999 |

\* cited by examiner

*Primary Examiner*—Julian W. Woo
*Assistant Examiner*—Sarah Webb
(74) *Attorney, Agent, or Firm*—James F. Crittenden

(57) ABSTRACT

A stent balloon assembly wherein the balloon has been blow molded inside the stent. Segments of the balloon at least partially fill gaps in the stent, even after the assembly is compressed, to retain the stent on the balloon during delivery. The stent balloon assembly may also be mounted on a catheter.

10 Claims, 2 Drawing Sheets

STENT BALLOON ASSEMBLY AND METHODS OF MAKING SAME

FIELD OF THE INVENTION

The invention relates to intraluminal stenting, and in particular, to an assembly of a stent and a balloon for delivery thereof. The stent balloon assembly may be mounted on a catheter.

BACKGROUND OF THE INVENTION

Intraluminal stenting is useful in treating tubular vessels in the body that are narrowed or blocked and it is an alternative to surgical procedures that intend to bypass such an occlusion. When used in endovascular applications, the procedure involves inserting a prosthesis into an artery and expanding it to prevent collapse of the vessel wall.

Percutaneous transluminal angioplasty (PTCA) is used to open coronary arteries, which have been occluded by a build-up of cholesterol fats or atherosclerotic plaque. Typically, a guide catheter is inserted into a major artery in the groin and is passed to the heart, providing a conduit to the ostia of the coronary arteries from outside the body. A balloon catheter and guidewire are advanced through the guiding catheter and steered through the coronary vasculature to the site of therapy. The balloon at the distal end of the catheter is inflated, causing the site of the stenosis to widen. Dilation of the occlusion, however, can form flaps, fissures or dissections, which may threaten, re-closure of the dilated vessel. Implantation of a stent can provide support for such flaps and dissections and thereby prevent reclosure of the vessel. Reducing the possibility of restenosis after angioplasty reduces the likelihood that a secondary angioplasty procedure or a surgical bypass operation will be necessary.

A stent is typically a hollow, generally cylindrical device formed from wire(s) or a tube and the stent is commonly intended to act as a permanent prosthesis. A stent is deployed in a body lumen from a radially contracted configuration into a radially expanded configuration, which allows it to contact and support the vessel wall. The stent can be made to be either radially self-expanding or expandable by the use of an expansion device. The self-expanding stent is made from a resilient material while the device-expandable stent is made from a material, which is plastically deformable. A plastically deformable stent can be implanted during an angioplasty procedure by using a balloon catheter bearing the compressed stent, which has been loaded onto the balloon. The stent radially expands as the balloon is inflated, forcing the stent into contact with the body lumen, thereby forming a support for the vessel wall. Deployment is effected after the stent has been introduced percutaneously, transported transluminally and positioned at a desired location by means of the balloon catheter.

A balloon of appropriate size and pressure may be first used to open the lesion. The process can be repeated with a stent loaded onto a balloon. A direct stenting procedure involves simultaneously performing angioplasty and stent implantation using a stent mounted on a dilatation balloon. After the balloon is withdrawn, the stent remains as a scaffold for the injured vessel.

SUMMARY OF THE INVENTION

The invention comprises a stent balloon assembly wherein the balloon has been blow molded inside the stent and the two elements are kept together thereafter. Alternatively, a stent form is positioned in the balloon mold and a balloon is blow molded into the stent form and then removed from the stent form and mold. A stent is then placed on the formed balloon. Segments of the balloon at least partially fill gaps in the stent, even after the stent and balloon assembly is compressed, to retain the stent on the balloon during delivery. The stent balloon assembly may also be mounted on a catheter.

BRIEF DESCRIPTION OF THE DRAWINGS

The present invention will be understood and appreciated more fully from the following detailed description taken in conjunction with the appended drawings in which.

The drawings are not to scale.

DETAILED DESCRIPTION OF THE INVENTION

Figure 1:
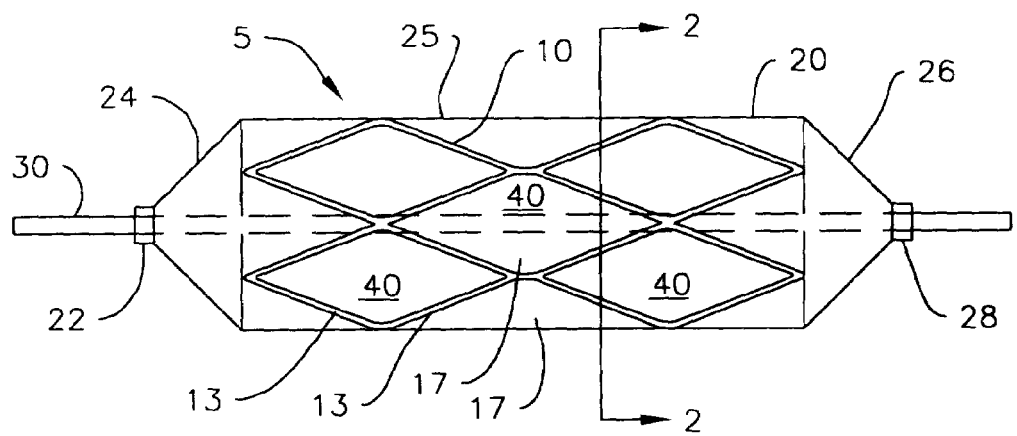
FIG. 1 is a longitudinal view of a stent balloon assembly mounted on a catheter in accordance with the invention, shown with the stent in an expanded configuration.

Applicant's invention is useful with any expandable stent, such as those stents designed for delivery by a balloon. FIG. 1 shows stent balloon assembly 5, including stent 10 and balloon 20 molded there within to intimately encapsulate stent 10 and retain stent 10 on catheter 30 during delivery. Stent 10 may be a generally cylindrical hollow tube defined by a pattern comprising solid portions 13 and gaps 17 formed there between. Stent 10 illustrates an example of a modular stent formed by a series of hoops having zigzag wire-forms, each hoop being joined to an adjacent hoop by its crowns or peaks. Any alternative stent design will function in the invention, as long as the stent is plastically deformable between an expanded configuration, shown in FIG. 1, and a compressed configuration, which will be described below in connection with FIGS. 6 and 7.

Alternative stent designs may be formed from wire-forms different from those of stent 10, including spiral zigzags, braids or a variety of other stents known to those of skill in the art of stents. Alternative stents may be made from slotted tubes or from perforated flat sheets that are rolled up into tubes. Stents within the invention may be formed of biocompatible metal, such as a stainless steel alloy, a refractory metal (e.g. tungsten or tantalum), or a precipitation hardenable alloy (e.g. MP35N or PH 455). Other metal combinations are also possible, such as one metal plated with another metal for improvements in biocompatibility and/or radiopacity. Biocompatible thermoplastic or thermoset polymers are also possible alternative materials for stents of the invention.

Stents within the invention may also incorporate any of a variety of coatings, as may be desired for enhanced friction or slipperiness, or for pharmaceutical reasons such as resistance to formation of blood clots or reduction of arterial restenosis. Alternative stents may also be support structures built into tubular prostheses such as vascular grafts, wherein the stent may have a graft mounted to the outside of the stent, the inside of the stent, or both. A precaution when choosing to use polymers, coatings or grafts with the stent of the invention is to carefully coordinate thermal properties of these materials with the thermal properties of the balloon polymer so that valuable characteristics of the stent are not ruined during the balloon blow molding process, which will be described below. To avoid possible damage to a stent coating during the balloon blow molding process, the stent and/or stent balloon assembly may be coated after the balloon has been formed within the stent. Another alternative in accordance with the invention is to coat the stent with a material that will thermally bond to the balloon when it is blow molded inside the stent.

As shown in FIG. 1, stent 10 is mounted on tubular balloon 20. Balloon body 25 may be generally cylindrical in shape, and it may be centrally located between proximal and distal frusto-conical sections 24, 26, respectively. Proximal and distal frusto-conical sections 24, 26 terminate in proximal and distal necks 22, 28, respectively, which are adapted to be mounted on catheter shaft 30. The transitions between body 25, frusto-conical sections 24, 26, and proximal and distal necks 22, 28 can be rounded or radiused, rather than the sharp delineations shown in FIG. 1. Balloon 20 is blow molded, or stretch blow molded inside of stent 10 to develop balloon segments 40 in gaps 17.

Balloon 20 may be molded by the same well known processes used for dilation balloons, such as angioplasty balloons, or for stent delivery balloons. In general, all such balloons are made from thermoplastic polymers such as polyvinyl chloride, polyolefins (e.g. polyethylene, irradiated polyethylene, polyethylene ionomer, polypropylene), polyester (e.g. polyethylene terephthalate), polyamide (e.g. nylon), polyurethane, ethylene-vinyl acetate, thermoplastic elastomer, other polymers that can be biaxially oriented to impart strength and from block copolymers (e.g. polyethylene block amide), blends and multi-layered combinations of the above polymers. Dilatation balloons may also be made from blends that include liquid crystal polymers.

It is well known in the art that a polymeric material that has been formed with a given shape can be subsequently processed to impart higher strength by stretching. During stretching, the molecular structure of the polymer is oriented so that the strength in that direction is higher. In a typical process of making a balloon, a polymer such as nylon or polyethylene block amide is first extruded into a tubular parison. The parison is subsequently heated to a temperature at which it softens. By pressurizing, or blowing the parison from inside and applying axial tension, circumferential and longitudinal stretching will form a biaxially oriented balloon. The balloon forming step should be performed above the glass transition temperature but below the melt temperature of the base polymer material. For polymer blends and other polymer combinations, such as block copolymers, the blowing temperature should be above the highest glass transition. The radial expansion and axial stretch step or steps may be conducted simultaneously, or depending upon the polymeric material of which the parison is made, following whatever sequence is required to form a balloon. To create high strength, thin walled balloons, it may be desired to stretch the thermoplastic material close to its elastic limit during processing. At the end of the balloon-making process, a heat setting step may be added, wherein heat and stretching are applied to the molded balloon. The conditions of the heat setting step maybe the same as or different from those used to initially form the balloon. The process of axial stretching and radial expansion is referred to as stretch blow molding.

Figure 8:
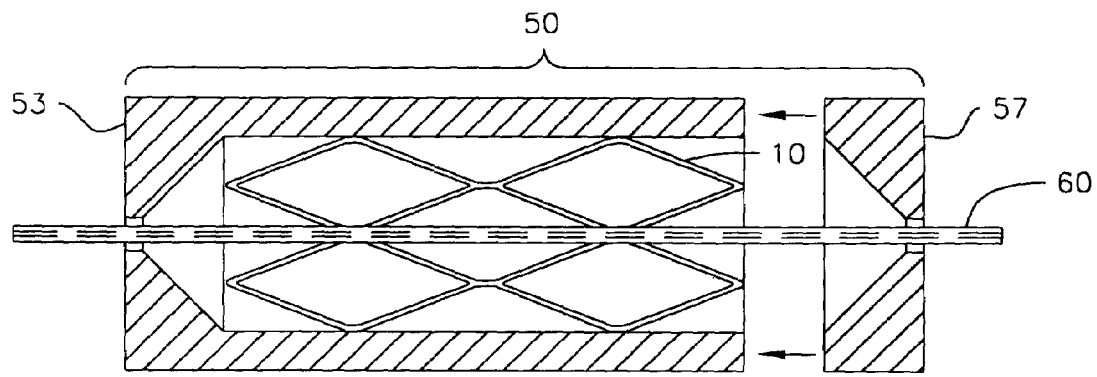
FIG. 8 is a longitudinal cross-sectional view of a stent and balloon parison in a split mold in accordance with the invention.

When stretch blow molding is carried out in a mold, which is optional, a balloon of predetermined shape and size can be made. To simplify mold fabrication and the removal of formed balloons, balloon molds are commonly split along one or more transverse planes, or they may be divided along a longitudinal axis. For example, FIG. 8 shows balloon mold 60, which has mold body 53, and removable end cap 57. This drawing is somewhat schematic, in that features employed to hold the mold together during balloon forming are absent. Also not shown are apparatuses that maybe used to pressurize and axially stretch balloon parison 60 and to heat and cool the mold. These components are well known in the art, and no specific variants thereof are critical to practicing the instant invention.

Figure 2:
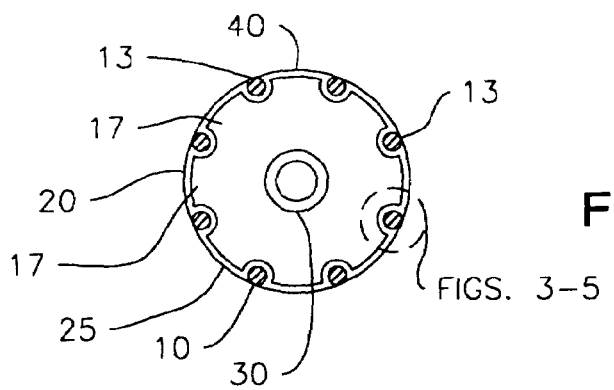
FIG. 2 is a transverse cross-sectional view along line 2B2 in FIG. 1.
Figure 5:
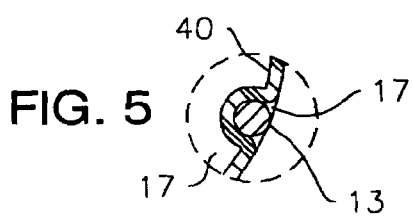
FIG. 5 is an enlarged view of another modified form of a portion indicated in FIG. 2.
Figure 4:
FIG. 4 is an enlarged view of a modified form of a portion indicated in FIG. 2.
Figure 3:
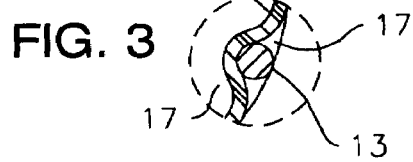
FIG. 3 is an enlarged view of a portion indicated in FIG. 2.

FIG. 2 illustrates a transverse cross-sectional view of stent balloon assembly 5, and shows segments 40 of balloon 20 having been molded into gaps 17 of stent 10. FIGS. 3–5 show, in magnified detail, how the edges of modified forms of segments 40 conform to stent solid portions 13. As described above, stent 10 is an example of a modular stent made from wire-form(s). Thus, in the cross-sectional views of FIGS. 2–5, stent solid portion 13 appears as a circular element. It is understood that alternative types of plastically deformable stents may have stent solid portions that are non-circular in cross-section. For example, a slotted tube stent (not shown) may have stent solid portions that are generally rectangular or trapezoidal in cross-section, as a result of the slotting process, whether it is laser cutting, chemical etching or other known methods. The extent to which balloon 20 forms about each stent solid portion 13 is determined by the relative dimensions of these two components, by the physical properties of the balloon material, and by the conditions of the balloon molding process.

FIG. 3, for example, shows balloon 20 having relatively minimal contact with stent solid portion 13 such that the edges of segments 40 are not wrapped substantially about stent solid portion 13. This form can result from balloon 20 having a relatively thick wall or relatively stiff material, or from the balloon molding conditions of temperature, time and internal pressure being inadequate to force the balloon material into more intimate engagement with stent solid portion 13.

FIG. 4 shows edges of segments 40 being molded roughly halfway around stent solid portion 13. Compared to the form shown in FIG. 3, this modified form maybe accomplished by balloon 20 having a relatively thinner wall or relatively more flexible material, or from the balloon molding conditions constituting relatively higher temperature, longer time and/or higher internal pressure.

FIG. 5 shows edges of segments 40 being molded almost three quarters of the way around stent solid portion 13. Again, as compared to the form shown in FIG. 4, this modified form may be accomplished by balloon 20 having an even thinner wall or more flexible material, or from the balloon molding conditions constituting higher temperature, longer time and/or higher internal pressure. If the final form of stent balloon 5 is as shown in FIG. 5, then FIGS. 3–5 may also be considered to show a progression of balloon deformation near the end of the molding process, proceeding from FIG. 3 to FIG. 4, and finally to FIG. 5. In such a case, the curved sector at the right side of FIGS. 3–5 would represent a cross-section of mold 60.

Figure 6:
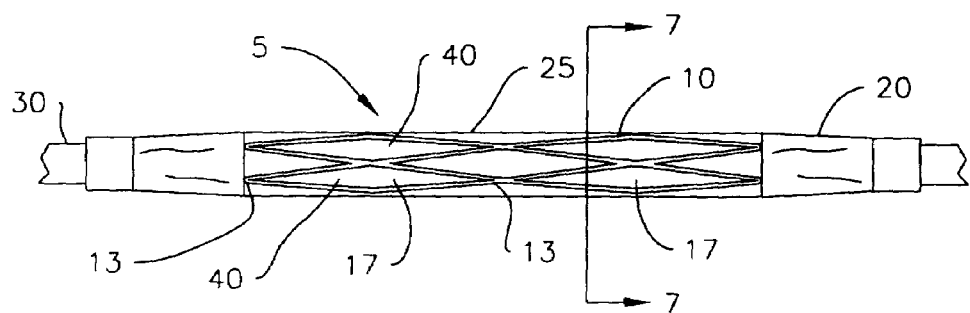
FIG. 6 is a longitudinal view of a stent balloon assembly mounted on a catheter in accordance with the invention, shown with the stent in a nearly compressed configuration.

FIG. 6 shows stent balloon assembly 5 having been contracted about catheter 30 into a nearly compressed configuration. Gaps 17 of stent 10 have been deformed from the open diamond shapes shown in FIG. 1 to more narrow diamond shapes approaching the form of a parallel-sided slot. As is well know in the art, the purpose of compressing stent 10 around catheter 30 is to reduce the profile of the entire assembly to enhance its passage through a patient's vessels and into a targeted treatment site. The plastic deformability of stent 10 will keep it in the compressed configuration about catheter 30 until balloon 20 is inflated at time of stent deployment in a patient.

Figure 7:
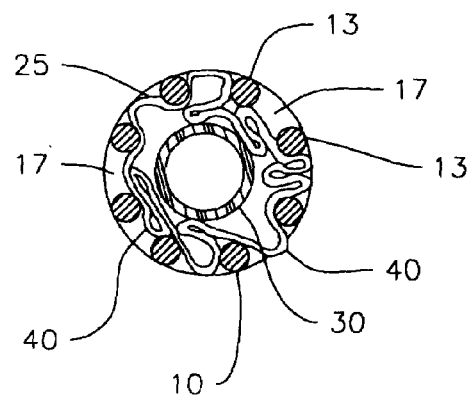
FIG. 7 is a transverse cross-sectional view along line 7B7 in FIG. 6, shown in larger scale.

FIG. 7 illustrates deformations that may take place in balloon 20 as stent 10 is compressed around catheter 30. As gaps 17 are reduced in area, balloon segments 40 are squeezed in from the edges where segments 40 have been molded into intimate contact with stent solid portions 13, as described above. Depending on the pattern of a stent in the invention, deformation of segments 40 may occur primarily in the circumferential direction. Typical stents are designed to have minimal change in length during transformation between compressed and expanded configurations. Gaps 17 typically have correspondingly minimal changes in length during such transformations. Consequently, longitudinal deformations in segments 40 are also typically minimal.

As shown in FIG. 7, some balloon segments 40 may be squeezed completely out of a gaps 17 into the space between stent 10 and catheter shaft 30, where segment 40 may fold over itself, and ultimately be crimped between stent 10 and catheter shaft 30. Other balloon segments 40 may be only partially squeezed out of gaps 17, leaving a some material of segments 40 within the deformed gaps 17. In such cases, some of the material of balloon segment 40 may be forced between stent 10 and catheter shaft 30, some material of balloon segment 40 may bulge radially outward from stent balloon assembly 5, and in some cases, material of balloon segment 40 will deform in both directions. In another alternative, balloon segments 40 may be squeezed into a zigzag pattern wherein most of the material of balloon segment 40 will remain in gaps 17. A combination of different types of balloon segment deformations is likely to take place during any given compression of stent 10 around catheter shaft 30. An optional method of controlling whether and to what extent balloon segments 40 may be squeezed inward or outward is to apply a selected fluid pressure or partial vacuum about or within balloon 20 while stent 10 is compressed about catheter shaft 30. Regardless of the combination of balloon segment deformations that takes place, the intimate encapsulation of balloon 20 into stent 10 by the balloon molding process ensures retention of stent 10 on balloon 20 during transluminal passage of stent balloon assembly 5 through the patient's vessels.

When stent balloon assembly 5 is inflated in a patient's treatment site, it will resume the expanded configuration in which it was formed, as shown in FIG. 1. Because stent 10 will be plastically deformed into the expanded configuration against the patient's vessel wall, deflation of balloon 20 will disengage it from its encapsulation with stent 10, which will remain implanted in the patient's vessel. In the alternative mentioned above, wherein balloon 20 has been molded into a thermal bond with a coating on stent 10, disengagement between balloon 20 and stent 10 at time of deployment will require breaking the bond, or peeling the coating from the stent for subsequent removal of the coating with the deflated balloon.

Stent balloon assembly 5 may be constructed in accordance with the following method. Mold 50 is provided, having mold body 53 and removable mold end cap 57. When mold body 53 and end cap 57 are held together, mold 50 comprises an internal cavity having the desired inflated shape of balloon 20. With end cap 57 removed from mold body 53, stent 10 is inserted, in its expanded configuration, into the cavity in mold 50. Tubular balloon parison 60 is provided and placed within mold 50 such that parison ends extend from both ends of mold 50 when body 53 and end cap 57 are held together. Typically, one parison end is sealed, as by clamping or melting, and the other parison end is connected to a pressure control apparatus. Selected pressure and axial tension are applied to parison 60 while mold 50 is raised to a selected temperature. In response to the physical and thermal molding conditions, balloon parison 60 expands within mold 50 against stent 10. Balloon parison 60 further deforms against solid portions 13 and through gaps 17 into contact with the cavity of mold 50. Thus, balloon 20 is blow molded into intimate encapsulation of stent 10, forming stent balloon assembly 5. After cooling mold 50 and stent balloon assembly 5 there within, and after releasing any remaining pressure applied to balloon 20, end cap 57 is detached from mold body 53 and stent balloon assembly 5 is removed there from. An alternative method of making stent balloon assembly 5 includes a stent form positioned within the mold 50. The stent form has the configuration of the stent that will be placed on the balloon. A balloon parison without a stent is placed in the mold and blow molded into the stent form and mold. The balloon is then removed leaving the stent form in the mold. A stent may then be placed on the balloon for forming a stent balloon assembly. The stent form may then be used for forming other balloons. This method may be preferably if the balloon forming process affects the stent or any coatings on the stent. Another alternate method includes mounting stent 10, in compressed configuration, around balloon parison 60 before inserting parison 60 into mold 50. In this case, proper selection of blow molding conditions such as temperature, pressure and tension, can result in stent 10 being plastically deformed against the mold cavity during formation of balloon 20.

To mount stent balloon assembly 5 onto catheter shaft 30, the molded ends of balloon 20 are typically trimmed to a desired length, forming proximal neck 22 and distal neck 28. Stent balloon assembly 5 is then slid over catheter shaft 30 and necks 22, 28 are then bonded thereto, as by adhesive, thermal bonding, laser bonding, or other suitable techniques that are well known to those skilled in the art of balloon catheters. Finally, stent balloon assembly 5 is crimped about catheter shaft 30, with stent 10 being plastically deformed into a compressed configuration, trapping balloon 20 between stent 10 and catheter shaft 30. As described above, at least portions of balloon segments 40 remain engaged with gaps 17 to securely retain stent 10 on balloon 20 until it is desired to deploy stent 10 within a patient's body.

While the invention has been particularly shown and described with reference to the embodiments and methods described above, it will be understood by those skilled in the art that various changes in form and detail may be made therein without departing from the spirit and scope of the invention. For example, during balloon molding, mold 50 can be heated by electrical elements, by immersion in a hot liquid, by use of a surrounding steam jacket, or by any other practical apparatus known to those skilled in the art of blow molding balloons.

We claim:

1. A method of making a stent balloon assembly comprising:
    providing a tubular stent being plastically deformable between a compressed configuration and an expanded configuration and having a pattern including solid portions and gaps formed there between;
    placing the stent, in the expanded configuration, within a balloon mold cavity;
    forming a balloon within the stent in the mold cavity by stretch blow-molding a parison of extruded thermoplastic tubing into a shape of the mold cavity such that one or more balloon segments at least partially fill the gaps in the stent pattern; and
    removing the balloon from the mold.

2. The method of claim 1 wherein forming the balloon includes stretch blow-molding the parison at a temperature above a glass transition temperature of the tubing.

3. The method of claim 1 wherein the stent and balloon are removed from the mold together.

4. The method of claim 3 further comprising mounting the stent and the balloon together about a distal portion of an elongate flexible catheter having a lumen providing fluid communication from a proximal end to an interior of the balloon.

5. The method of claim 3 further comprising deforming the stent into the compressed configuration such that at least some of the segments of the balloon remain partially filling the gaps.

6. The method of claim 1 wherein the balloon is capable of deforming the stent from the compressed configuration to the expanded configuration.

7. The method of claim 1 wherein the tubing comprises a bi-axially oriented thermoplastic material.

8. The method of claim 7 wherein the thermoplastic material is selected from a group consisting of polyvinyl chloride, polyamides, polyolefins, polyesters, polyurethanes, ethylene-vinyl acetate, block co-polymers, liquid crystal polymers, and blends and multi-layered combinations of the same.

9. The method of claim 1 wherein the balloon comprises a generally cylindrical body having proximal and distal necks joined thereto by frusto-conical sections.

10. A method of making a stent balloon assembly comprising:
    providing a mold having a cavity shaped to form a cylindrical balloon with frusto-conical end sections;
    providing a tubular stent having a pattern including solid portions and gaps formed there between, the stent being plastically deformable between a compressed configuration and an expanded configuration sized to fit within the mold cavity;
    placing the stent, in the expanded configuration, within the mold cavity;
    placing an extruded tubular parison through the stent within the mold;
    stretch blow-molding the parison into contact with the mold cavity to form a balloon intimately encapsulating the stent; and
    removing the stent balloon assembly from the mold.

* * * * *